United States Patent [19]
Pirani et al.

[11] Patent Number: 5,699,162
[45] Date of Patent: Dec. 16, 1997

[54] PROCESS AND APPARATUS FOR TESTING A MULTI-TRIP BOTTLE FOR CONTAMINATION UTILIZING RESIDUAL LIQUID IN BOTTLE BOTTOM AND SPRECTRAL MEASUREMENT

[75] Inventors: Peter Pirani, Grüt; Martin Rosatzin, Embrach; Daniel Wildmann, Dielsdorf, all of Switzerland

[73] Assignee: Elpatronic AG, Zug, Switzerland

[21] Appl. No.: 554,445

[22] Filed: Nov. 7, 1995

[30] Foreign Application Priority Data

Nov. 28, 1994 [CH] Switzerland ............ 03 578/94

[51] Int. Cl.⁶ ............ G01N 21/00; G01N 9/04; G01N 21/25; B07C 5/00
[52] U.S. Cl. ............ 356/427; 356/240; 356/409; 250/223 B; 209/587; 209/588; 209/577; 209/583; 235/383
[58] Field of Search ............ 356/427, 240, 356/409; 250/223 B, 223 R; 209/524, 576–577, 580–581, 583, 588, 587; 235/383

[56] References Cited

U.S. PATENT DOCUMENTS

| | | | |
|---|---|---|---|
| 4,830,192 | 5/1989 | Plester et al. | 209/577 |
| 4,858,768 | 8/1989 | Plester | 209/577 |
| 4,998,824 | 3/1991 | Littlejohn et al. | 356/409 |
| 5,002,397 | 3/1991 | Ingrum et al. | 356/409 |
| 5,067,616 | 11/1991 | Pleester et al. | 209/577 |
| 5,216,239 | 6/1993 | Yoshida | 356/240 |
| 5,361,912 | 11/1994 | Krieg et al. | 356/240 |
| 5,405,014 | 4/1995 | Krieg et al. | 209/577 |
| 5,443,164 | 8/1995 | Walsh et al. | 356/240 |
| 5,612,525 | 3/1997 | Apler et al. | 235/383 |

FOREIGN PATENT DOCUMENTS

| | | |
|---|---|---|
| A-0 557 814 | 9/1993 | European Pat. Off. |
| A-4 200 971 | 7/1993 | Germany. |
| A-2 258 915 | 2/1993 | United Kingdom. |
| WO-A-8 800 862 | 2/1988 | WIPO. |

*Primary Examiner*—Frank G. Font
*Assistant Examiner*—Jason D. Vierra Eisenberg
*Attorney, Agent, or Firm*—McCormick, Paulding & Huber

[57] ABSTRACT

To test a bottle for contamination, the bottom of the bottle is laterally illuminated with a measuring light beam from a source. This measuring light beam is deflected, as if in a waveguide, in the ring of residual liquids at the bottom of the bottle. Light reemerging from the residual liquid is imaged on a detector by an imaging lens. The detector measures the spectral composition of the deflected light and compares this with theoretical values which should be yielded by the liquid with which the bottle was last filled. If deviations from the theoretical values are excessive, the bottle is rejected. The process described provides a simple way of determining whether a multi-trip bottle has contained an extraneous liquid.

10 Claims, 1 Drawing Sheet

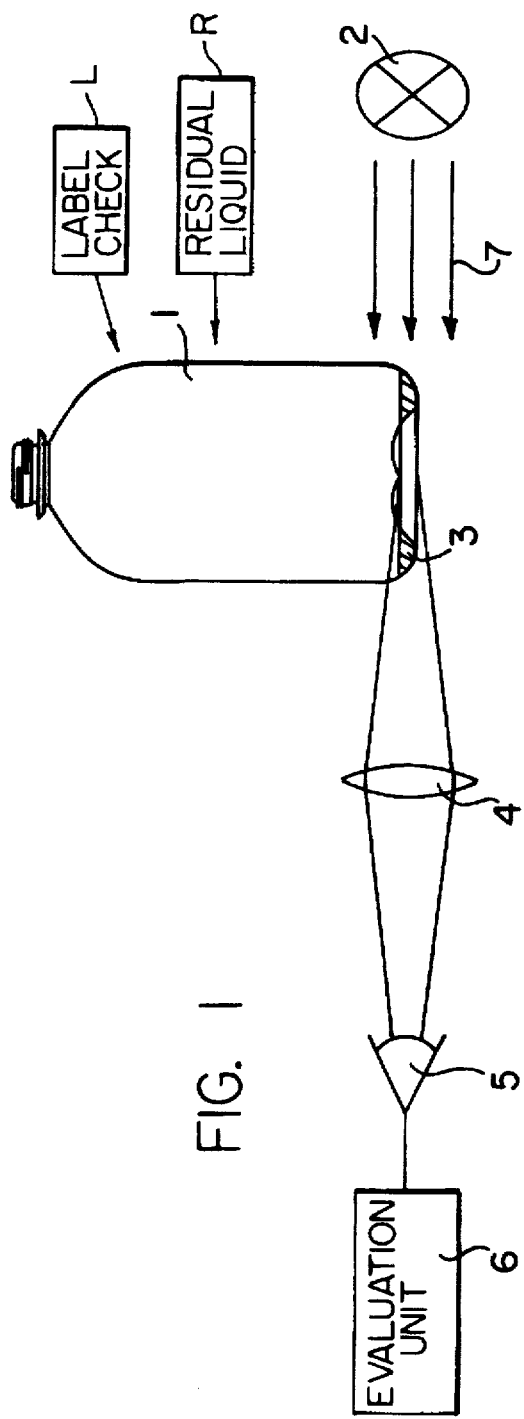
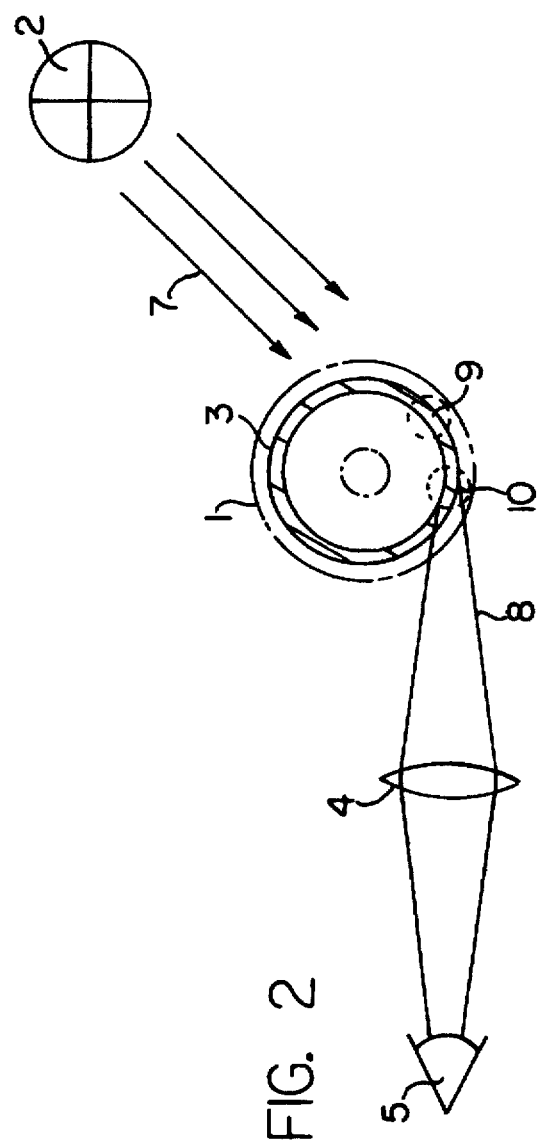

PROCESS AND APPARATUS FOR TESTING A MULTI-TRIP BOTTLE FOR CONTAMINATION UTILIZING RESIDUAL LIQUID IN BOTTLE BOTTOM AND SPRECTRAL MEASUREMENT

BACKGROUND OF THE INVENTION

The invention relates to a process for testing a multi-trip bottle, in particular a multi-trip PET bottle, for contamination, and also an apparatus for carrying out the process, in accordance with the introductory clauses of the independent claims.

If bottles are reused, especially plastic bottles, returned bottles need to be tested for the presence of contaminants which might taint the product to be inserted. This is normally done by taking readings of the gaseous phase in the interior of the bottle, e.g. by chemical analyses, infrared spectroscopy or mass spectroscopy. However, there exist some contaminants which cannot be detected in this way and which nevertheless are capable of tainting the product to be inserted.

This poses the task of providing a process and/or an apparatus capable of detecting contaminants which cannot be traced, or can be traced only with difficulty, by current methods.

SUMMARY OF THE INVENTION

Measuring optical properties of residual liquid present in the bottle may reveal contaminants which cannot be detected in the gaseous phase. Preferably a region of the bottom of the bottle is illuminated and the light transmitted is subjected to spectral analysis, for example to determine its colour. The optical properties of the residual liquid can be compared with theoretical values. Bottles which contain residual liquids with optical properties which do not correspond to those of the liquid with which the bottle was last filled are normally rejected.

To enable testing to include bottles containing a very small amount of residual substances, or residues which have dried out, a diluting liquid may be injected before the reading is taken. This diluting liquid may for example be water, or a colourless aqueous solution, e.g. caustic solution.

The detector is preferably positioned at an angle to the main emission direction of the light source. This angle is about 20° to 70°, and preferably 45° to 55°. Since the residual liquid increases the dispersion and/or refraction of the measuring beam, the specific sensitivity of the process can be enhanced. Such an arrangement is particularly suitable for bottles in which the residual liquid collects in a ring at the bottom. Here, the measuring beam is coupled tangentially into the liquid ring, where it is at least partly conveyed by total reflection, in the manner of an optical waveguide. Depending on the bottle type, the light emerges at a specific angle or more than about 20°. The emerging light is preferably imaged on to the detector by means of a 1:1 lens.

BRIEF DESCRIPTION OF THE DRAWINGS

Further advantages and applications of the invention will emerge from the following description with reference to the drawings, in which:

FIG. 1 is a side view of the residual liquid testing set-up; and

FIG. 2 shows the set-up in FIG. 1 viewed from above.

DESCRIPTION OF THE PREFERRED EMBODIMENTS

Multi-trip bottles coming back from the consumer to the bottling plant usually contain a few milliliters of liquid residues, or residues which have dried out. So long as these liquid residues correspond to the liquid with which the bottle was originally filled, no problems arise. However bottles containing residues of other, unknown liquids need to be eliminated before being reused. In the process according to the invention, the colour of the residual liquid is compared with the colour of the liquid with which the bottle was originally filled. For example, lemon-flavoured drinks are usually colourless, while those with an orange flavour are orange-coloured, and colas have the characteristic brownish colour.

In the process according to the invention, the bottles are first of all run through a label checking stage L. This determines, for example on the basis of the colour of the label, the type of liquid with which the bottle was originally filled. Theoretical values for the subsequent readings are determined on the basis of these data.

This label check can be omitted if there is another means of knowing what kind of drink was previously contained in the bottles.

In a next step, a diluting liquid can be inserted into the bottles, as the optical measuring method requires a minimum quantity of residual liquid of e.g. 5 milliliters. For this purpose, an injection stage R may be provided. This may introduce diluting liquid into all the bottles, or only into those containing less than 5 milliliters of residual liquid. Examples of suitable diluting liquids are water or caustic solution.

Alternatively, all bottles containing an insufficient quantity of residual liquid may be excluded from the testing process.

The bottle is then fed to the optical measuring apparatus which is illustrated schematically in FIGS. 1 and 2.

Here the bottle 1 is placed in the beam of light 7 from a light source 2 by means of a suitable positioning device which is not shown.

In bottles with a well-formed bottom dome and an annular base, the residual liquid 3 is contained in an annular region at the bottom of the bottle, as can be seen in FIG. 2 in particular. The bottle is positioned so that the essentially parallel light from the source 2 impinges tangentially on a region 9 of the ring of residual liquid 3. The incident light 7 is coupled into the ring of residual liquid 3, as in an optical waveguide. In the residual liquid 3, the light is repeatedly refracted and totally reflected. Depending on the bottle type, it then emerges in a zone 10 at an angle of e.g. approx. 45° to 55° to the axis of the incident light beam.

A 1:1 imaging lens 4 images the merging light 8 onto a detector 5. The detector 5 spectrally analyses the light received in the IR and/or UV and/or visible wavelength ranges, for example by measuring the total light output in specific wavelength ranges, or by sampling the power spectrum density over a given wavelength range.

Light emerging unrefracted through the bottom of the bottle in the incident direction is not fed to the detector 5. This increases the sensitivity of the process, as the residual liquid and its characteristics have a greater effect on the intensity and spectral distribution of the deflected light than on those of the undeflected light.

An electronic evaluation unit 6 coupled to the detector 5 compares the distribution coefficients obtained for the emerging light 8 with the theoretical values determined at the outset. If deviation from the theoretical values is excessive, the bottle is rejected.

The system according to the invention can, of course, also be combined with conventional methods (e.g. spectroscopy in the gaseous phase) in order to increase the reliability of detection still further.

We claim:

1. Process for testing a multi-trip bottle for contamination, the bottle having a bottom region with an annular base, a domed center portion and a vertically-oriented axis so that residual liquid collects in a ring in the bottom region comprising the steps of:

illuminating the bottom region of the bottle by a light source, so that a light beam extending from the source in a first direction generally tangent to the annular base is incident on the bottom region, a portion of the light beam being conveyed by reflection through the liquid and partially around the ring and emerging from the bottom region generally in a second direction generally tangent to the annular base, the first and second directions lying in a plane oriented generally perpendicular to the bottle axis; and spectrally-analyzing a portion of the light beam emerging in the second direction.

2. Process according to claim 1, wherein the angle between the emerging light beam which is analyzed during the step of analyzing and the incident light beam is between about 20° to 70°.

3. Process according to claim 1, wherein the angle between the emerging light beam which is analyzed during the step of analyzing and the incident light beam is 45° to 55°.

4. Process according to claim 1, wherein the bottle has a label, further comprising the steps of:

checking a label on the bottle and determining required values for the optical properties of the residual liquid based upon the label, and comparing values corresponding to the spectrally-analyzed light with the required values.

5. Process according to claim 1, further comprising the step of injecting a quantity of diluting liquid in the bottle so that a minimum quantity of residual liquid is present in the bottle before the step of measuring the optical properties.

6. Process according to claim 1, further comprising the step of checking to determine whether a minimum quantity of residual liquid is present in the bottle.

7. Apparatus for testing a multi-trip bottle for contamination, the bottle having a bottom region with an annular base, a domed center portion and a vertically-oriented axis so that residual liquid collects in a ring in the bottom region, comprising:

a light source to produce a measuring light beam extending from the source directed in a first direction toward and generally tangent to the annular base is incident on the bottom region of a bottle, a portion of the light beam being conveyed by reflection through the liquid and partially around the ring and emerging from the bottom region generally in a second direction generally tangent to the annular base, the first and second directions lying in a plane oriented generally perpendicular to the bottle axis and a detector for spectral analysis of a portion of the light beam emerging from the bottle in the second direction.

8. Apparatus according to claim 7, wherein the detector has an imaging lens.

9. Apparatus according to claim 7, wherein the detector is positioned along the second direction at an angle of 20° to 70° to the first direction.

10. Apparatus according to claim 9, wherein the angle is between about 45° to 55°.

* * * * *